(12) United States Patent
Al-Qaffas

(10) Patent No.: US 8,316,496 B2
(45) Date of Patent: Nov. 27, 2012

(54) DENTAL HYGIENE DEVICE

(76) Inventor: Qasem Al-Qaffas, Al-Diyah (KW)

( * ) Notice: Subject to any disclaimer, the term of this patent is extended or adjusted under 35 U.S.C. 154(b) by 512 days.

(21) Appl. No.: 12/565,906

(22) Filed: Sep. 24, 2009

(65) Prior Publication Data

US 2011/0067194 A1 Mar. 24, 2011

(51) Int. Cl.
*A61C 17/22* (2006.01)
(52) U.S. Cl. .................................. 15/22.1; 15/23; 15/28
(58) Field of Classification Search ................. 15/22.1, 15/23, 28
See application file for complete search history.

(56) References Cited

U.S. PATENT DOCUMENTS

| | | | | |
|---|---|---|---|---|
| 1,616,484 A * | 2/1927 | Beynon | ........................ | 15/167.2 |
| 2,292,707 A * | 8/1942 | Mantell | ........................ | 15/167.1 |
| 2,701,380 A * | 2/1955 | Ripper | ........................ | 15/167.2 |
| 3,732,589 A * | 5/1973 | Burki | ........................ | 15/22.1 |
| 4,223,417 A * | 9/1980 | Solow | ........................ | 15/22.1 |
| 5,177,826 A * | 1/1993 | Vrignaud et al. | ........................ | 15/22.1 |
| 5,669,097 A * | 9/1997 | Klinkhammer | ........................ | 15/167.1 |
| 5,876,206 A * | 3/1999 | Maurer | ........................ | 433/216 |
| 6,625,834 B2 * | 9/2003 | Dean | ........................ | 15/27 |
| 7,036,180 B2 * | 5/2006 | Hanlon | ........................ | 15/167.2 |
| 7,676,875 B2 * | 3/2010 | Cho | ........................ | 15/27 |
| 7,832,043 B1 * | 11/2010 | Feldman | ........................ | 15/28 |
| 7,958,588 B2 * | 6/2011 | Ukaj | ........................ | 15/28 |
| 2002/0152563 A1 * | 10/2002 | Sato | ........................ | 15/22.1 |
| 2007/0204413 A1 * | 9/2007 | Kuznetsov et al. | ........................ | 15/22.2 |
| 2008/0216257 A1 * | 9/2008 | Ahadpour et al. | ........................ | 15/22.1 |

FOREIGN PATENT DOCUMENTS

| WO | 2010/039112 | * | 4/2010 |
|---|---|---|---|
| WO | 2010039112 | * | 4/2010 |

* cited by examiner

*Primary Examiner* — Mark Spisich
*Assistant Examiner* — Michael Jennings
(74) *Attorney, Agent, or Firm* — Richard C. Litman

(57) ABSTRACT

A toothbrush for brushing the bite surface and two sides of a tooth simultaneously including a handle and three brush head connected to the handle. The head assembly includes three brushes that are rotated about 3 parallel vertical axis while the assembly itself is rotatable about an angle of at least 180° so that a single brush cleans/polishes the inner surface of the teeth in the individual's mouth as the assembly is moved from one side of the individual's mouth to the other side.

6 Claims, 10 Drawing Sheets

DENTAL HYGIENE DEVICE

FIELD OF THE INVENTION

This invention relates to a dental hygiene device and more particularly to a rotary toothbrush for brushing the bite surface and both sides of a tooth simultaneously.

BACKGROUND FOR THE INVENTION

Toothbrushes for cleaning multiple teeth at the same time have been known for many years. For example a U.S. Pat. No. 4,224,710 of Solow discloses a power-actuated toothbrush that brushes both sides of a tooth. The bristles extend at an angle to the sides of the tooth so that the bristles enter and clean the sulcus area. As disclosed, the bite surface of the teeth are cleaned simultaneously with the sides of the teeth and at times an entire dental arch or even the entire mouth of teeth can be cleaned in a single operation.

A second approach for simultaneously cleaning multiple teeth is disclosed in a U.S. Pat. No. 4,313,237 wherein a toothbrush has an electric motor enclosed in a handle for driving a plurality of rotary brushes for simultaneously cleaning multiple tooth surfaces. The rotary brushes are mounted in a brush head adapted to be releasably supported on one end of an elongated brush head support stem having flexible drive shafts extending there along and having its other end adapted to be releasably mounted on the handle to provide a rotary driven connection between the motor and brushes. The releasable mounting of the brush head and its support stem enables hygienic use of the same motor and handle by a plurality of persons through use of personalized snap-on brush heads and support stems and also makes possible the ease and economical replacement of the brush heads.

A further approach to a dental hygiene apparatus having a plurality of rotating brushes is disclosed in U.S. Pat. No. 4,538,315 of Barth. As disclosed therein, a dental hygiene apparatus having five incurvated, flexible, rotating brushes mounted in a H-shaped arrangement on a housing which comprises an open brush holder portion matching with two opposed half dental arches and consists of an outer cheek-guard and an inner tongue-guard, and a closed biting portion provided with a pair of opposite restrictions for receiving the incisor teeth of the other two half dental arches.

In addition, a U.S. Pat. No. 5,177,826 of Vrignaud et al. discloses a powered toothbrush with a pair of disc-like rotary brushes mounted for rotation about an axis generally perpendicular to the length of the brush. The rotary brushes are in axially spaced relationship and are provided with inwardly directed bristles. Between the rotary brushes, upper and lower linear brushes are mounted above and below the axis of rotation for linear reciprocating motion generally perpendicular to that axis. The upper brush has upwardly directed bristles, and the linear brushes are mounted to the rotary brushes so as to be brought into reciprocal, linear movement when the rotary brushes are reciprocated angularly.

Further, a patent of Arnoux et al., U.S. Pat. No. 5,864,911 discloses a toothbrush with a dual rotary brushing system. The patent discloses a mechanical toothbrush with dual rotary brushing systems and comprising a handle forming body and a head fixed to the handle. The head is provided with two adjacent contra-rotating brushes of cylindrical shape and having substantially parallel axes. Each of the two brushes is driven by a flexible shaft situated in the head and supported at least at its distal end, by a respective bearing mounted on a support that enables the two brushes to move apart one away from the other, then urging the brushes towards the other by a return effect.

A still further approach to a rotary tooth cleaning device is disclosed in the U.S. Pat. No. 6,343,396 of Simovitz et al. The Simotivtz et al. patent discloses a tooth cleaning device having a tooth cleaning head including: (i) a housing with sides that straddle the tooth along both long faces and defining a longitudinal axis extending between the sides thereof and along the long faces; (ii) gears affixed along respective inner surfaces of the sides of the housing; (iii) tooth cleaning elements affixed along the inner side of the gears and being operatively spaced apart from one another, along the longitudinal axis of the tooth cleaning head, to form a gap therebetween; and (iv) a drive mechanism including: a drive shaft affixed to the inner surfaces of the sides of the housing and spanning the housing, a drive wheel connected to the drive shaft, and transfer gears affixed near the ends of the drive shaft and aligned with the gears; and (b) a handle connected to the tooth cleaning head, wherein as the tooth cleaning device travels along a row of teeth, the drive wheel rotates along the biting surface of the teeth, thereby rotating the drive shaft and the transfer gears, the transfer gears in turn providing rotating motion to the gears affixed along the inner surfaces of the sides of the housing and the tooth cleaning elements, such that the long faces of the tooth are cleaned simultaneously by rotary cleaning motion.

Notwithstanding the above it is presently believed that there is a need and a potential commercial market for an improved dental hygiene device in accordance with the present invention. There should be a need and a potential market for such devices because the device cleans the bite surface and both sides of a tooth simultaneously and is adapted to move from one tooth to another around the dental arches until the upper or lower teeth are cleaned. The action is then repeated for the upper or lower dental arches which were not cleaned in the first action. Further, the dental hygiene device as disclosed is relatively inexpensive to manufacture and can be sold at a competitive price. The device also includes a battery operated motor in the handle for driving the brushes to effect the cleaning action. Further, it is believed that the devices in accordance with the present invention can be manufactured and sold at a competitive price, are relatively durable and manufactured in a way that the brushes can be readily replaced.

BRIEF SUMMARY OF THE INVENTION

A toothbrush for brushing the bite surface and both sides of a tooth simultaneously comprises and/or consists of a longitudinally extending handle and a three brush assembly disposed at one end of the handle. The three brush assembly includes a pair of spaced apart bristles disposed on a common generally horizontal axis and adapted to engage both sides of a tooth and rotatable about the axis. The device also includes a third rotatable brush disposed between the pair of brushes and rotatable about a vertical axis for cleaning the bite surface of the tooth.

In addition the toothbrush in accordance with the present invention includes means for simultaneously rotating the brushes about their respective axis while the assembly of brushes may be rotated to an angle of at least about 180° about the generally vertical axis. In this way a brush engaging an inner side of a tooth on a first side of a first dental arch will engage an inner side of a tooth on an opposite side of an individual's mouth when the handle moves the three brush assembly from one side of the patient's mouth to an opposite side of the patient's mouth. In fact, the movement of the handle will pass the brushes over the front teeth where the inner brush will remain on the inner side of the front teeth.

The invention will now be described in connection with the accompanying drawings wherein like reference numerals have been used to indicate like parts.

DESCRIPTION OF THE PREFERRED EMBODIMENTS OF THE INVENTION

Figure 1:
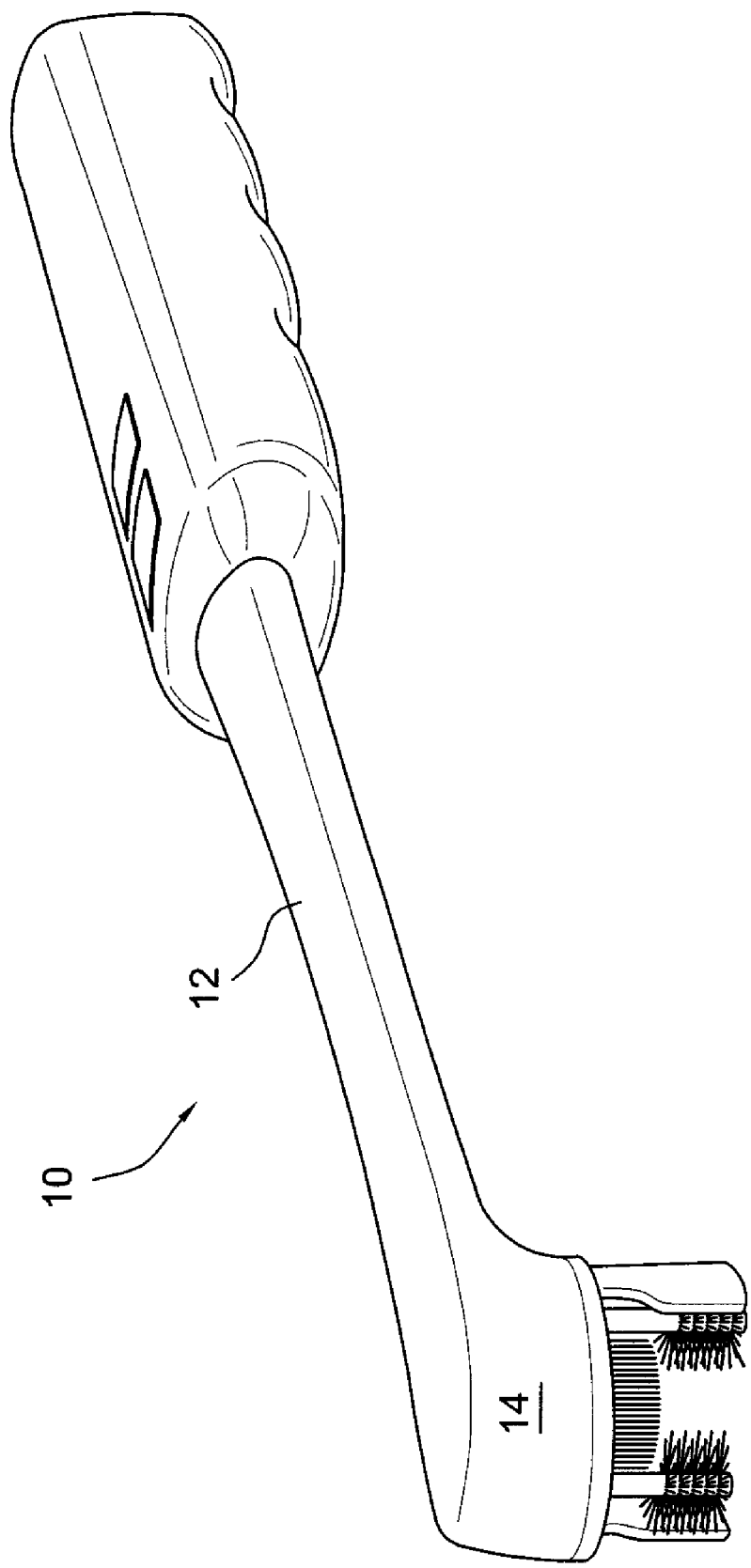
FIG. 1 is a perspective view of an improved rotary toothbrush in accordance with the present invention.
Figure 2:
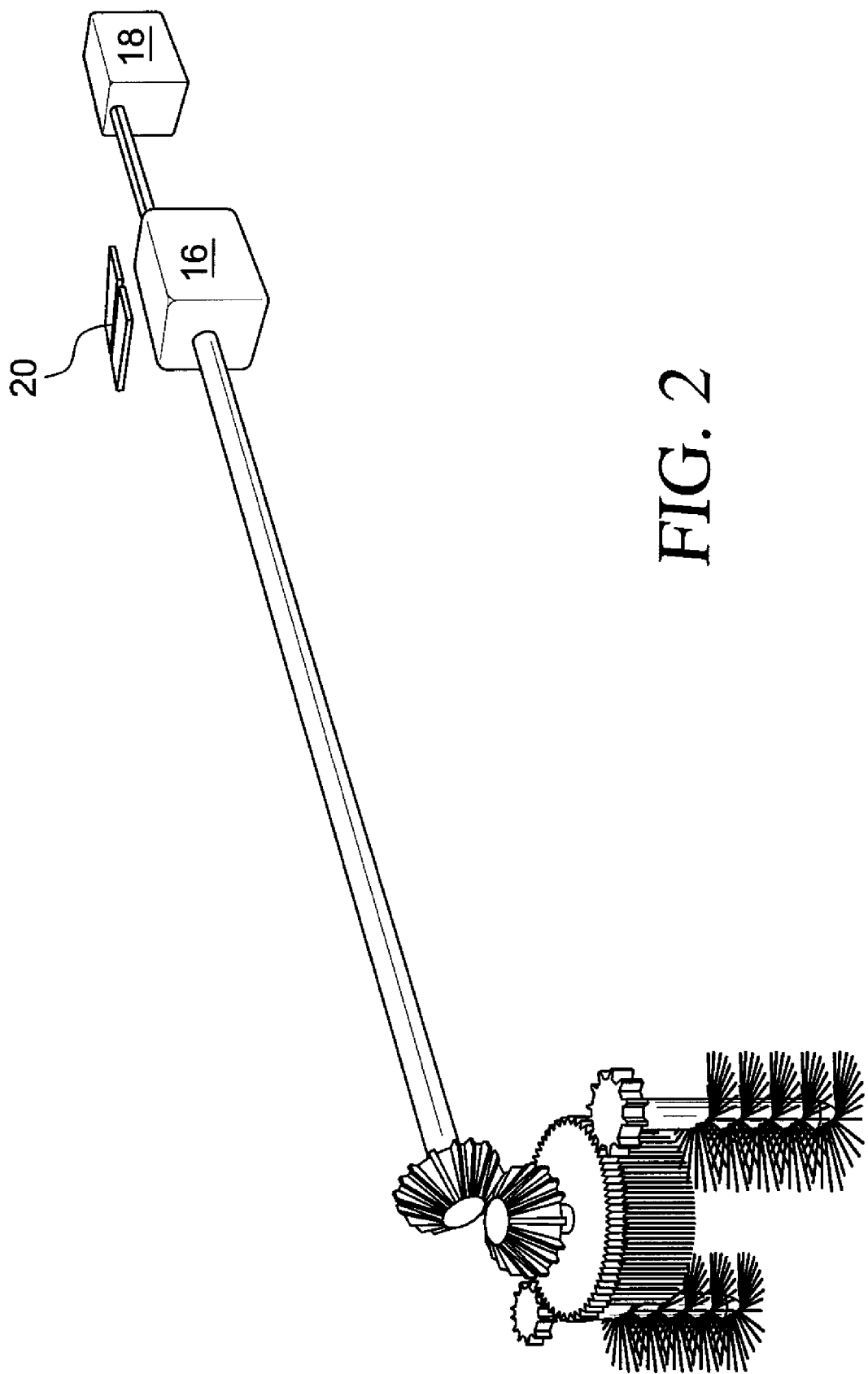
FIG. 2 is a perspective view of the mechanical components of the rotary brush shown in FIG. 1.
Figure 3:
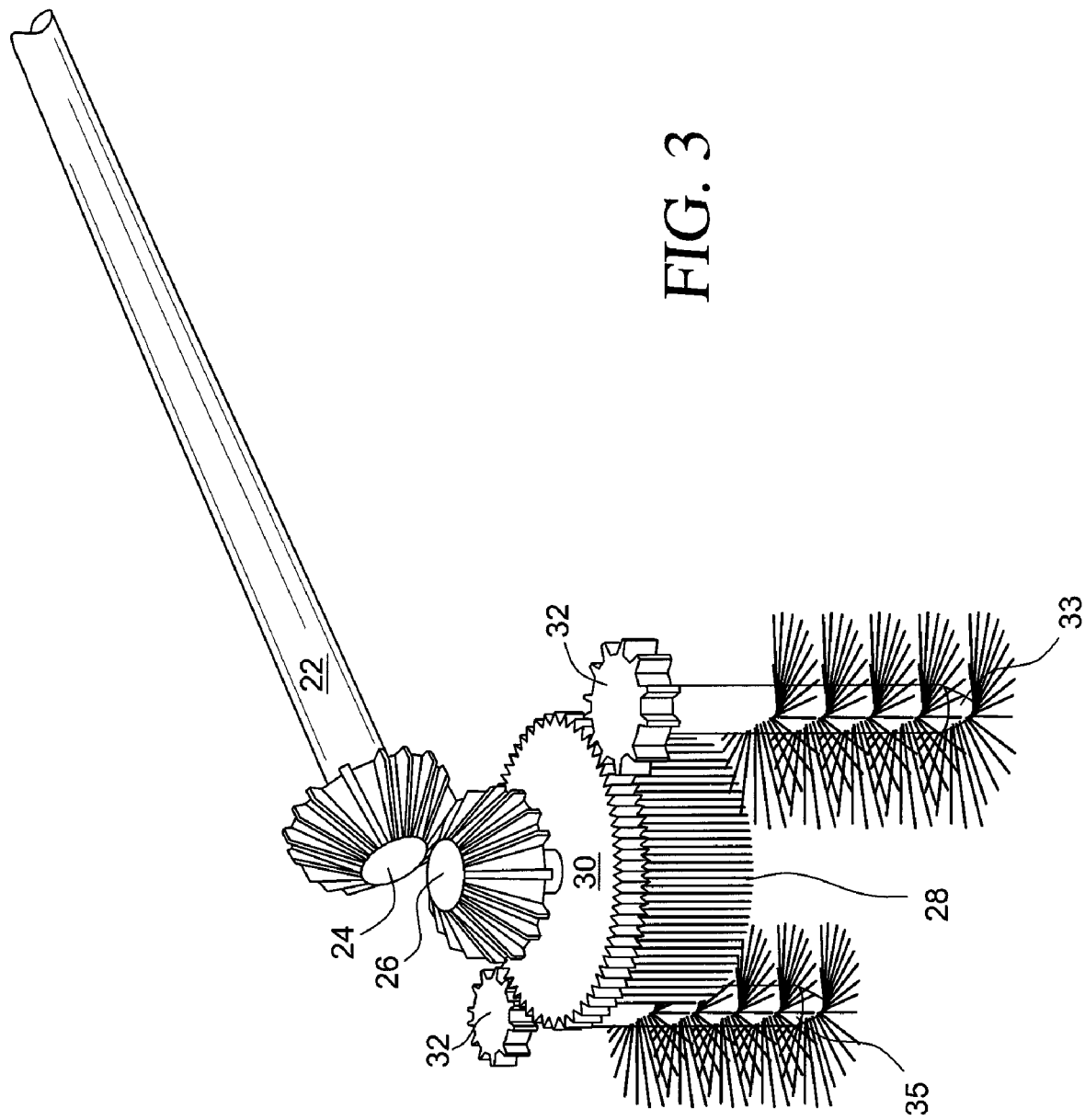
FIG. 3 is a perspective view of a brush head assembly in accordance with the present invention.
Figure 4:
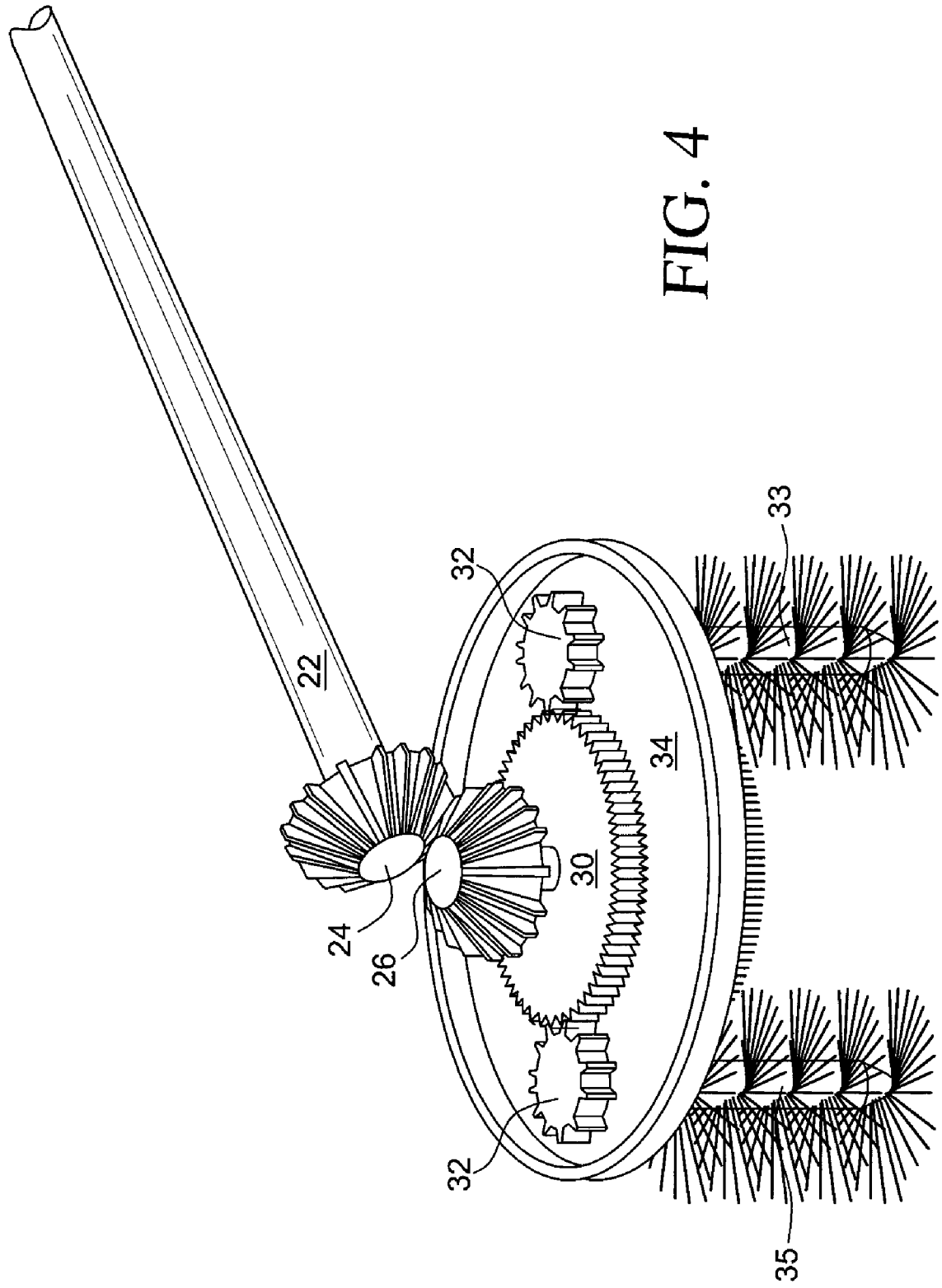
FIG. 4 is a perspective view of the brush head assembly shown in FIG. 3 but including a disc element for separating the distances between the two brushes that rotate about a vertical axis.
Figure 5:
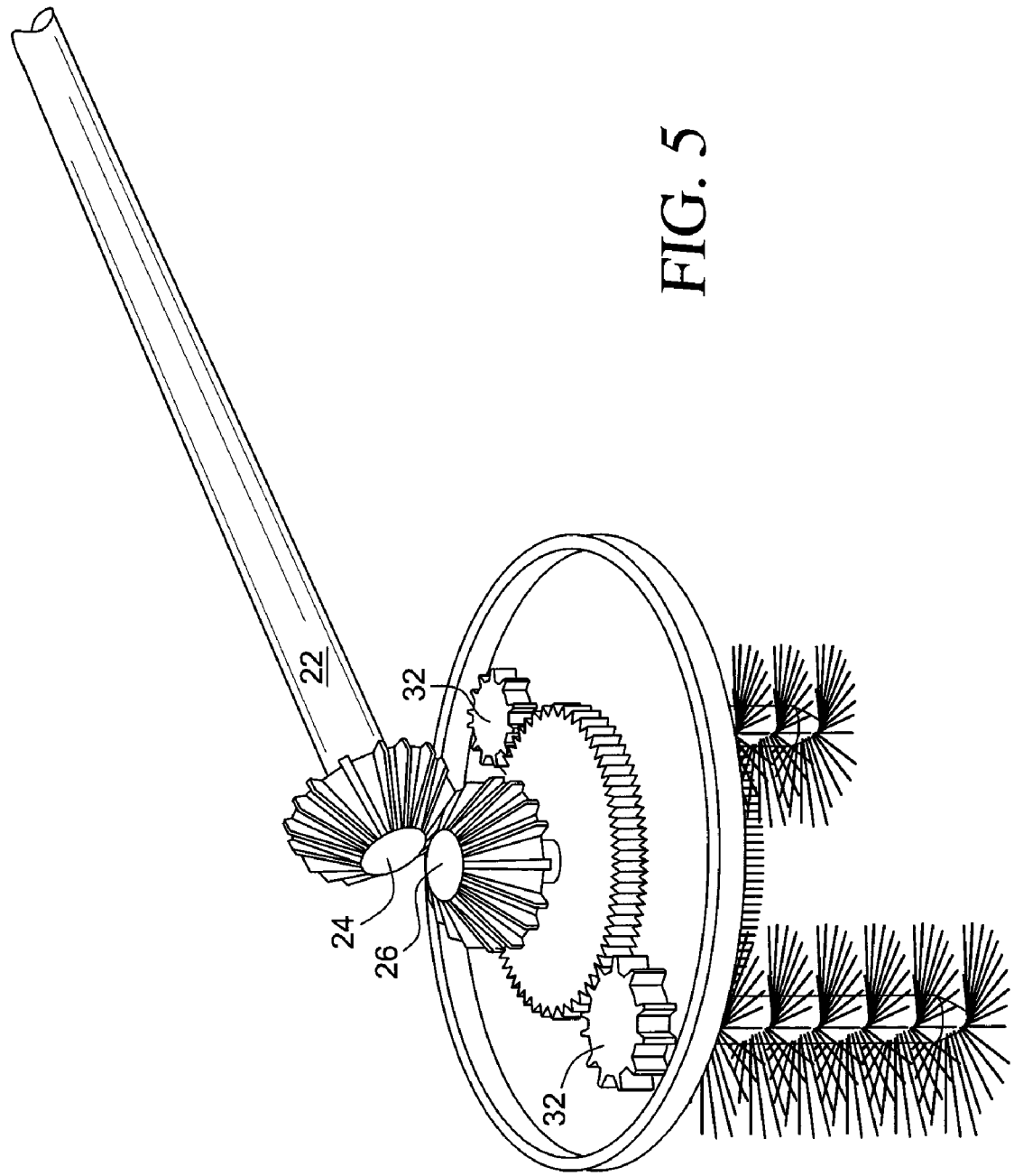
FIG. 5 is a second perspective view from a different angle showing the position of the brushes as the brush assembly is moved from the side teeth to a front tooth.

An improved rotary brush 10 in accordance with a preferred embodiment of the invention will now be described in accordance with FIGS. 1-10. Referring now to FIGS. 1-5, the rotary toothbrush 10 includes a longitudinally extending handle 12 with a multi-brush head assembly 14. The handle 12 also include a motor 16, rechargeable battery 18 and switch 20 that include an on/off switch and speed selector (See FIG. 2). An output of the motor 16 is connected to a shaft 22 that extends to the head assembly 14 and is connected thereto by a drive or bevel gear 24 that meshes with a driven bevel gear 26.

The bevel gears 24 and 26 transfer rotational movement along a generally horizontal axis to rotational movement along a vertical axis and rotate an intermediate brush 28 and sun gear 30. The sun gear 30 meshes with two pinions or planetary gears 32 that rotate a pair of brushes 33 and 35 about two spaced apart vertical axis so that the brushes 33 and 35 simultaneously can clean both sides of a tooth while the intermediate brush 28 simultaneously cleans the bite surface of the same tooth. A plastic disc 34 positions the brushes 33 and 35 with respect to one another, while permitting rotational movement of the brushes 33 and 35 as the brush assembly is moved from one side of an individual's mouth to the opposite side thereof.

Figure 6:
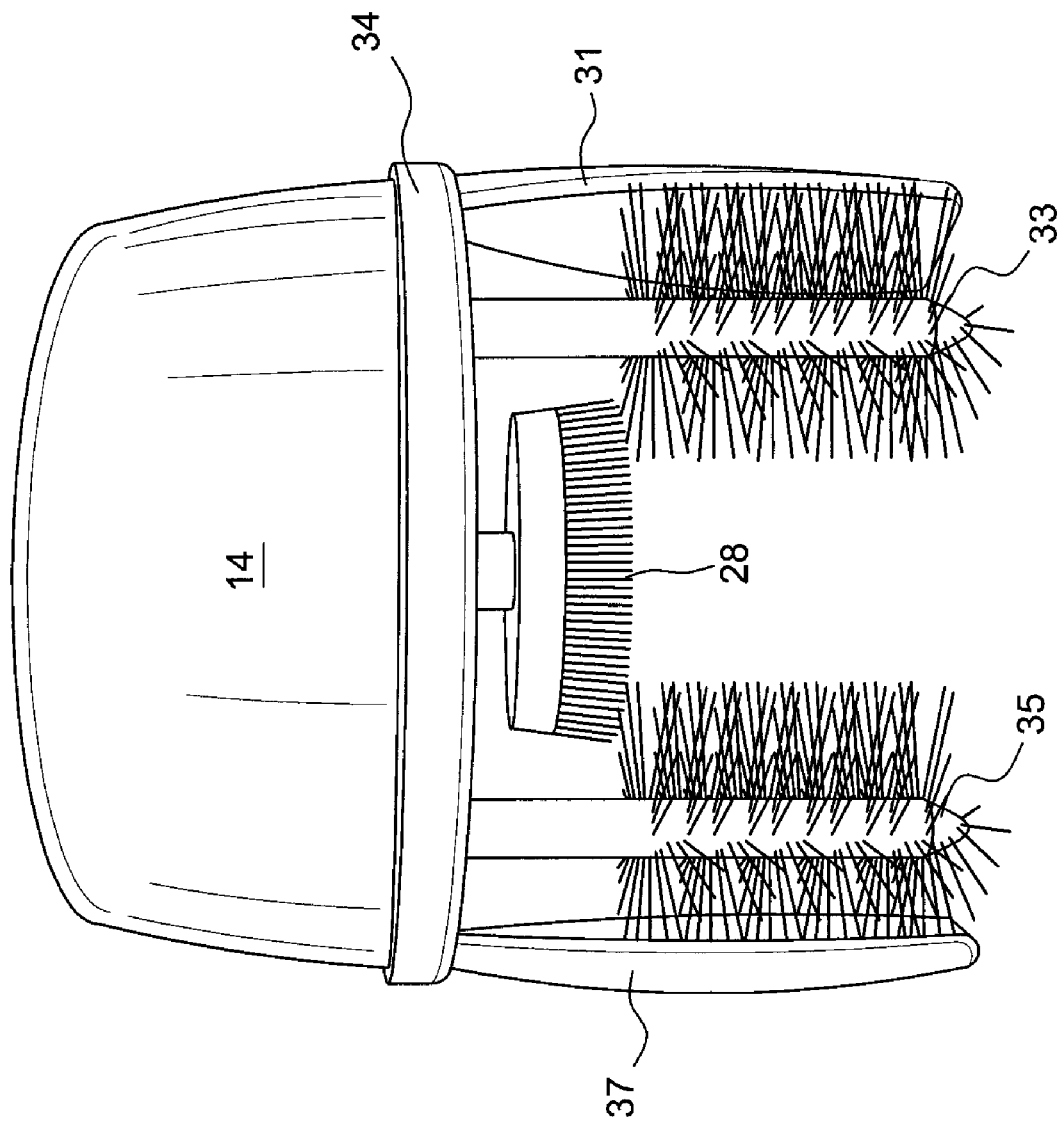
FIG. 6 is a side elevational view showing the pair of brushes and intermediate brush together with a pair of brush guards to protect the inside of a patient's mouth and tongue from the abrasion of the brushes.

FIG. 6 illustrates the difference in bristle lengths between the brushes 33 and 35 as compared to the intermediate brush 28. As shown, the intermediate brush 28 has relatively short, thicker and harder bristles than brushes 33 and 35. These harder short bristles are more effective in removing food particles from the bite surfaces of a tooth. As shown in FIG. 6 the disc 34 also carries a pair of mouth guards for protecting an individual's inner cheeks and tongue from abrasion by the brushes 33 and 35.

Figure 7:
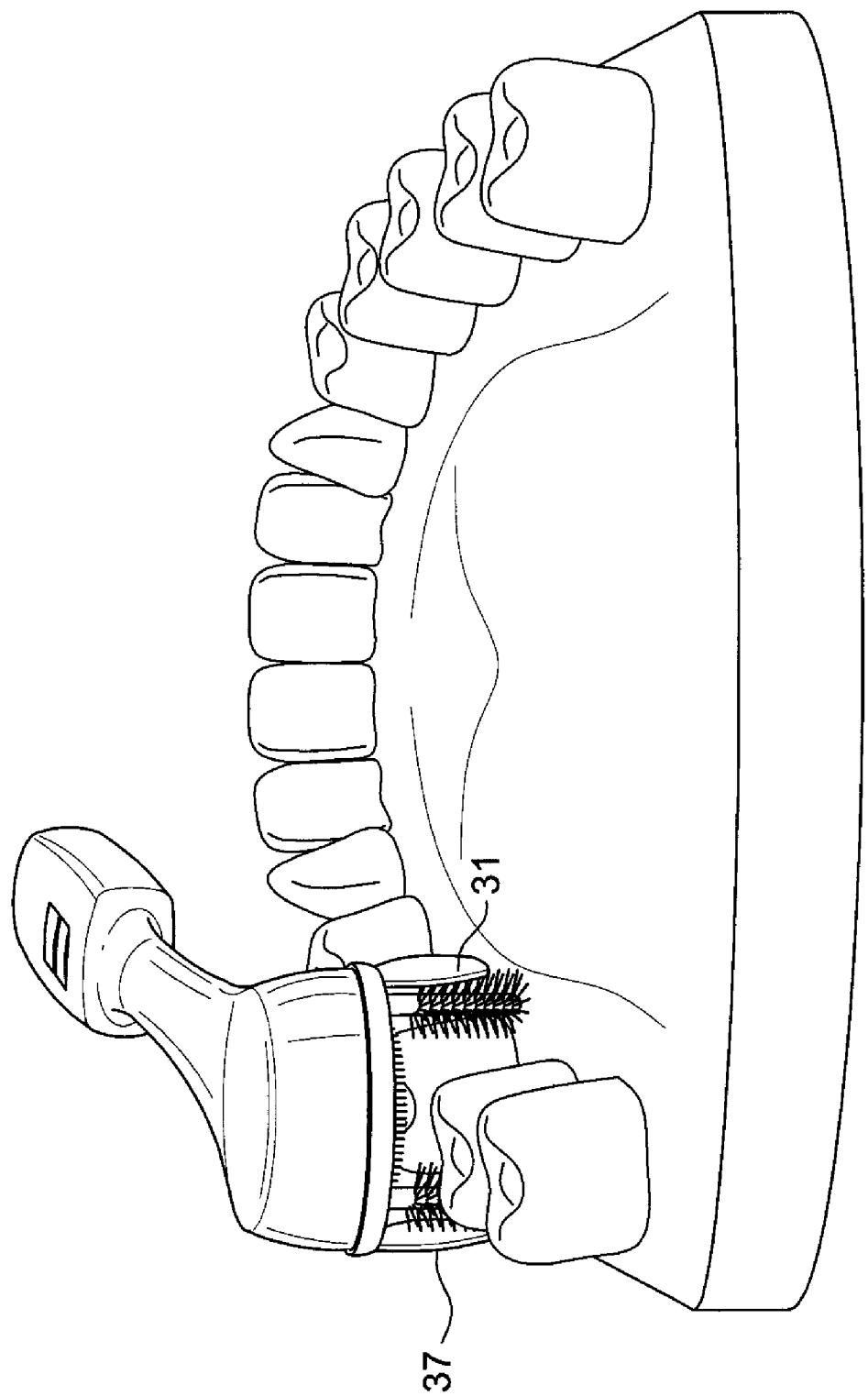
FIG. 7 is a perspective view of a lower set of teeth showing the brush assembly as it is used on one side of the mouth.
Figure 8:
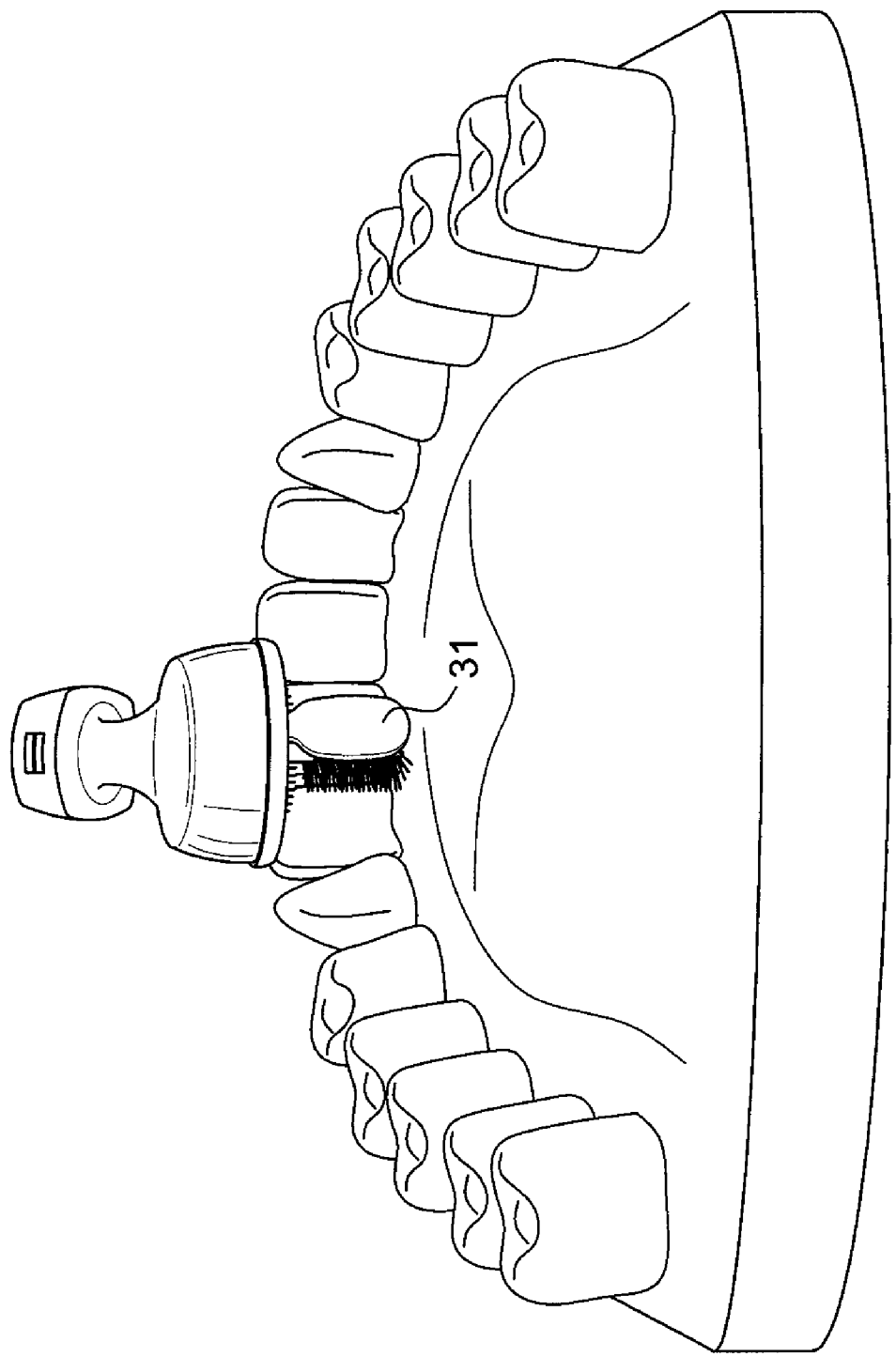
FIG. 8 is a perspective view illustrating the use of a brush in accordance with the present invention on the lower front teeth of an individual.
Figure 9:
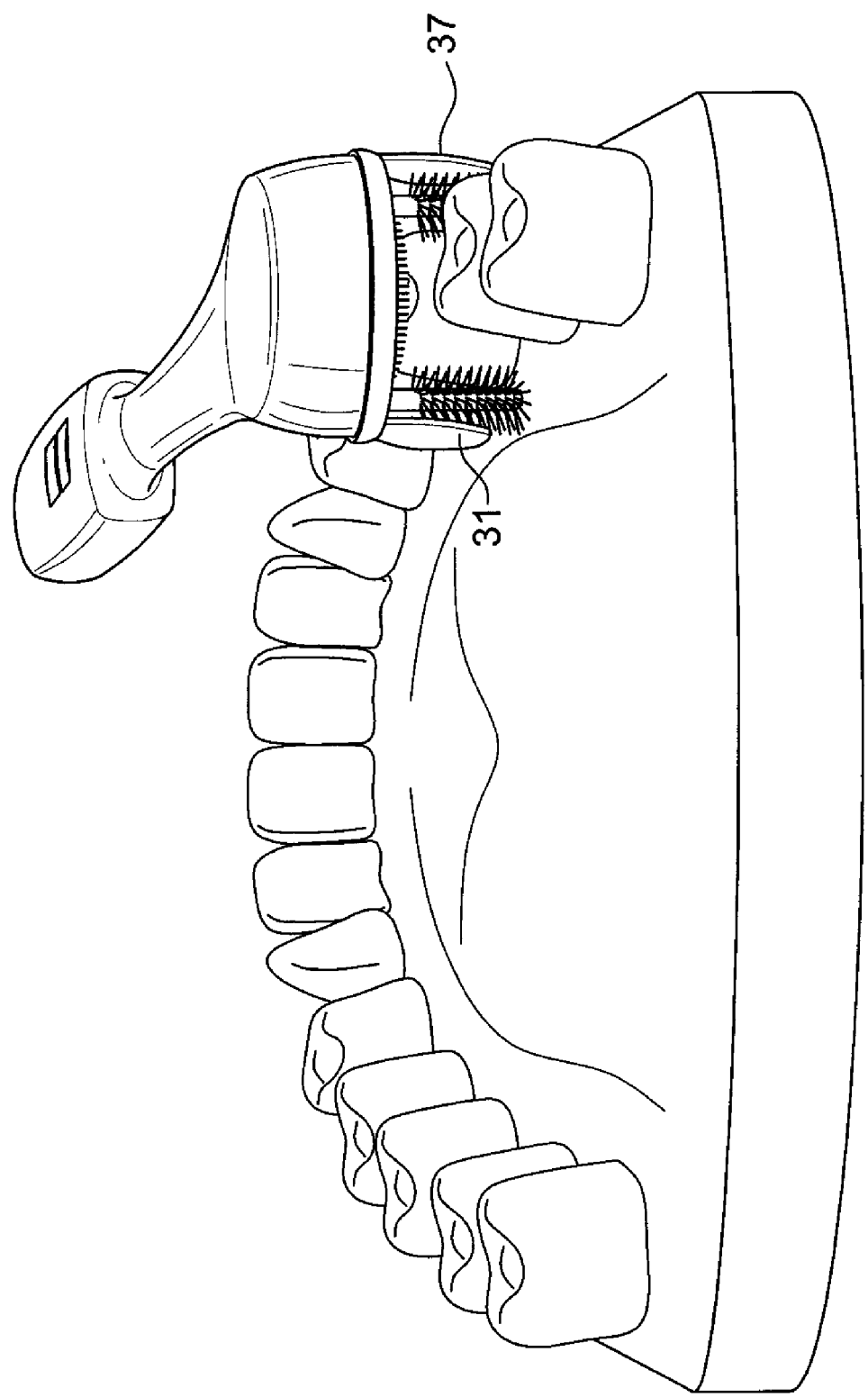
FIG. 9 is a perspective view illustration the use of a brush in accordance with the present invention on the lower right portion of an individual's mouth.
Figure 10:
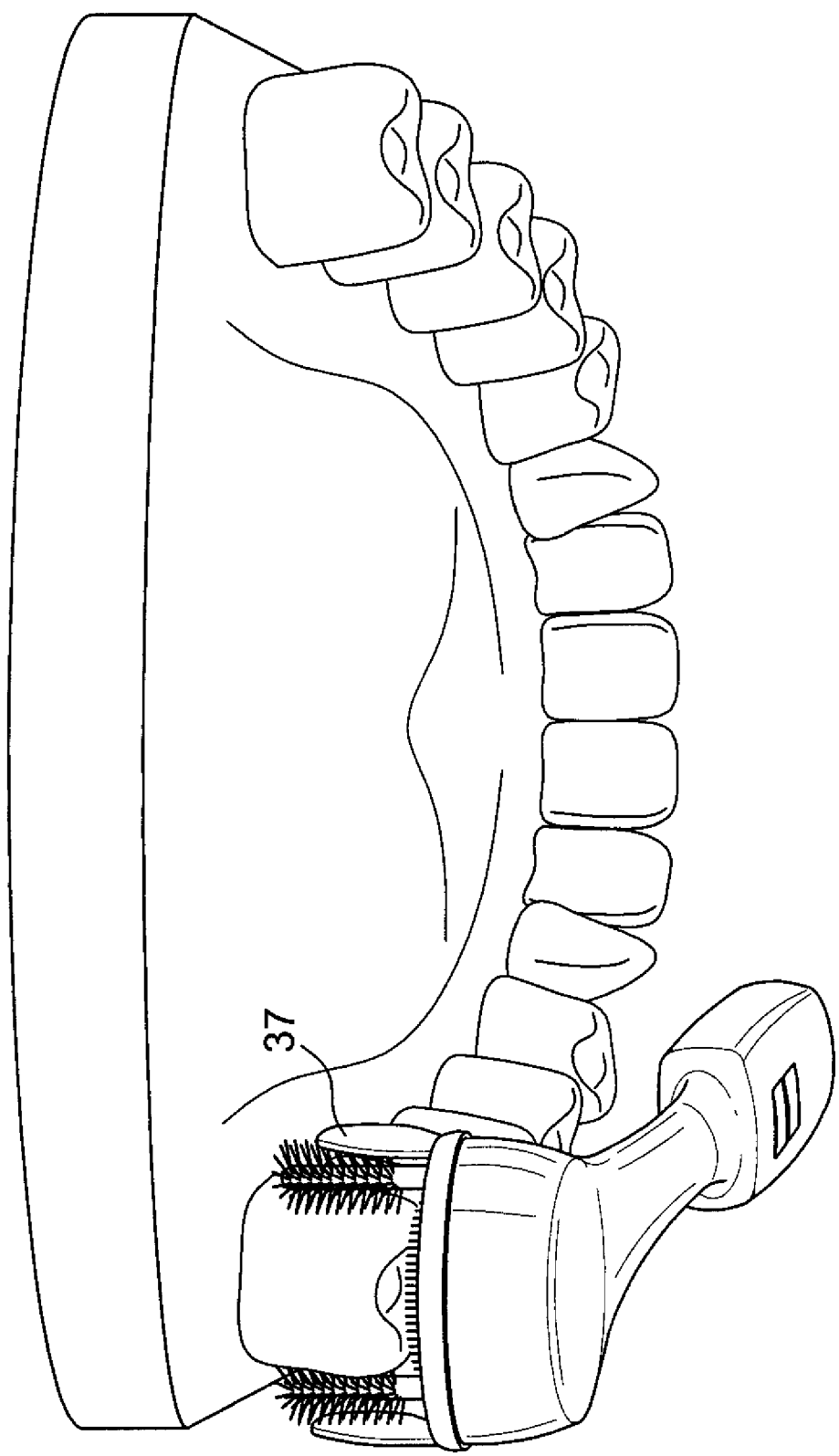
FIG. 10 is a perspective view illustrating the use of the brush assembly in accordance with the present invention on an upper portion of an individual's mouth.

The use of a brush in accordance with the present invention will now be described in connection with FIGS. 7-10. For example, FIG. 7 illustrates a starting point for cleaning the lower molars when a first brush 33 is being used to clean an inside surface while brush 35 cleans the outer surface and brush 28 cleans the bite surface of the same tooth. Then as the toothbrush handle is moved to clean the front teeth, the brushes 33 and 35 will be rotated to polish the sides of the front teeth i.e. the front and back surfaces thereof. The brushes 33 and 35 each have a brush guard 31 and 37 respectively for protecting an inner portion of an individual's mouth and tongue from the rotating brushes.

While the invention has been described in connection with its preferred embodiments it should be recognized that changes and modifications may be made therein without departing from the scope of the appended claims.

What is claimed is:

1. A toothbrush for brushing the bite surface and both sides of a tooth simultaneously, said toothbrush comprising:
a longitudinally extending handle and a three brush assembly disposed at one end of said handle;
said three brush assembly including a pair of spaced apart brushes disposed on generally vertical axes and adapted to engage both sides of a tooth, wherein the bristles of said pair of spaced apart brushes are:
i) spaced about their respective vertical axis,
ii) oriented radially to their respective vertical axis,
iii) define a first length, and
iv) possess a first hardness,
a third rotatable brush disposed between said pair of brushes and rotated about a parallel vertical axis for cleaning the bite surface of a tooth, wherein the third brush is located adjacent the upper bristles of said pair of brushes and possesses bristles oriented parallel to the parallel vertical axes and define a second length shorter than the first length and a second hardness greater than the first hardness; and
means for simultaneously rotating said brushes about their respective axis while rotating said assembly of brushes through an angle of at least 180 degrees about a generally vertical axis.

2. A toothbrush for brushing the bite surface and both sides of a tooth simultaneously according to claim 1, wherein the means for simultaneously rotating said brushes includes a battery and a battery powered motor disposed in said handle.

3. A toothbrush for brushing the bite surface and both sides of a tooth simultaneously according to claim 2 in which said three brushes are operatively connected to said motor by a shaft and bevel gear assembly.

4. A toothbrush for brushing the bite surface and both sides of a tooth simultaneously according to claim 3 in which said handle includes a switch for energizing said motor.

5. A toothbrush for brushing the bite surface and both sides of a tooth simultaneously according to claim 4 in which said motor is a multi-speed motor and in which a switch disposed in said handle is used to select the speed of said motor.

6. A toothbrush for brushing the bite surface and both sides of a tooth simultaneously according to claim 5 which includes a mouth and tongue guard to protect the cheeks and tongue from abrasion by one of the brushes.

* * * * *